United States Patent [19]

Nomura et al.

[11] Patent Number: 5,597,562

[45] Date of Patent: Jan. 28, 1997

[54] ORAL DOSAGE FORM OF BIOLOGICALLY ACTIVE PROTEINS

[75] Inventors: Hideaki Nomura, Takasaki; Kazutoshi Maruyama, Maebashi, both of Japan

[73] Assignee: Kirin-Amgen, Inc., Thousand Oaks, Calif.

[21] Appl. No.: 167,721

[22] Filed: Dec. 15, 1993

Related U.S. Application Data

[63] Continuation of Ser. No. 994,076, Dec. 17, 1992, abandoned, which is a continuation of Ser. No. 709,622, Jun. 3, 1991, abandoned.

[30] Foreign Application Priority Data

Jun. 1, 1990 [JP] Japan .................................. 2-145231
May 24, 1991 [JP] Japan .................................. 3-149737

[51] Int. Cl.$^6$ .......................... A61K 45/05; A61K 9/64; A61K 38/19; A61K 38/22
[52] U.S. Cl. .................. 424/85.1; 424/456; 424/457; 424/460; 424/491; 424/499; 514/2; 514/8; 514/12; 514/21
[58] Field of Search ................... 424/85.1, 456, 424/499, 457, 460, 491; 514/2, 12, 8, 21

[56] References Cited

U.S. PATENT DOCUMENTS

| | | | |
|---|---|---|---|
| 3,909,444 | 9/1975 | Anderson et al. | 428/402.24 |
| 4,156,719 | 5/1979 | Sezaki et al. | 424/118 |
| 4,182,330 | 1/1980 | Michaels | 424/473 |
| 4,572,915 | 2/1986 | Crooks | 514/458 |
| 4,703,008 | 10/1987 | Lin et al. | 435/240.2 |
| 4,806,524 | 2/1989 | Kawaguchi et al. | 514/8 |
| 4,849,227 | 7/1989 | Cho | 424/498 |
| 4,882,164 | 11/1989 | Ferro et al. | 424/450 |
| 4,961,926 | 10/1990 | Gabrilove | 424/85.1 |
| 4,985,404 | 1/1991 | Mitchell | 514/6 |
| 4,994,439 | 2/1991 | Lohgenecker et al. | 514/3 |
| 5,071,964 | 12/1991 | Dustin et al. | 530/395 |
| 5,206,219 | 4/1993 | Desai | 514/3 |

FOREIGN PATENT DOCUMENTS

| | | |
|---|---|---|
| 178576 | 4/1986 | European Pat. Off. . |
| 178665 | 4/1986 | European Pat. Off. . |
| 225189 | 6/1987 | European Pat. Off. . |
| 263490 | 4/1988 | European Pat. Off. . |
| 266119 | 5/1988 | European Pat. Off. . |
| 3723781 | 1/1988 | Germany . |
| 61091131 | 5/1986 | Japan . |
| 61097229 | 5/1986 | Japan . |
| 62089627 | 4/1987 | Japan . |

(List continued on next page.)

OTHER PUBLICATIONS

Chien et al., *J. Pharm. Sci.*, 78(5), 376–383 (1989).
Manzoni et al., *Pharmacological Res.*, 21(1), 105–106 (1989).
Miyake et al., *J. Biol. Chem.*, 252(15), 5558–5564 (1977).
Nishihata et al., *J. Pharm. Pharmacol.*, 33, 334–335 (1981).
Ritschel et al., *Res. Commun. Pathol. Pharmacol.*, 63(1), 53–67 (1989).
Saffran et al., *Science*, 233, 1081–1084 (1986).

(List continued on next page.)

*Primary Examiner*—Robert A. Wax
*Assistant Examiner*—William W. Moore
*Attorney, Agent, or Firm*—Marshall, O'Toole, Gerstein, Murray & Borun

[57] ABSTRACT

An oral dosage form comprising: (a) granulocyte colony stimulating factor or erythropoietin; (b) surfactant(s); (c) fatty acid(s); and (d) enteric material. The oral drug preparations provided by the present invention avoid inactivation of the principal ingredient during the process of pharmaceutical manufacturing and display enhanced absorption of the ingredient from the intestinal tract, particularly as a result of the addition of fatty acid(s) to the drug composition. As such, oral dosage forms of the present invention can allow for dosage reductions, facilitate accurate dose control, and increase the practical usefulness of the bioactive proteins.

13 Claims, 4 Drawing Sheets

FOREIGN PATENT DOCUMENTS

| | | |
|---|---|---|
| 63091325 | 4/1988 | Japan . |
| 63146826 | 6/1988 | Japan . |
| 63146827 | 6/1988 | Japan . |
| 63146828 | 6/1988 | Japan . |
| 63146829 | 6/1988 | Japan . |
| 63152326 | 6/1988 | Japan . |
| 63190833 | 8/1988 | Japan . |
| 63500636 | 12/1988 | Japan . |
| 217156 | 4/1990 | Japan . |
| 2177914 | 2/1987 | United Kingdom . |
| 2193631 | 2/1988 | United Kingdom . |
| 8905624 | 6/1989 | WIPO . |
| 9001329 | 2/1990 | WIPO . |

OTHER PUBLICATIONS

Ueno et al., *Chem. Pharm. Bull.*, 30(6), 2245–2247 (1982).

Welte et al., *Proc. Natl. Acad. Sci. USA*, 82, 1526–1530 (1985).

Wigley et al., *Diabetes*, 20(8), 552–556 (1971).

Merck Index, Tenth Edition, p. 1055 (1983).

Takada, K., et al., Chem. Pharm. Bull., vol. 37, No. 3, pp. 838–839, Mar. 1989.

Carmichael, R. D., et al., Biol. Neonate, vol. 33, pp. 119–131, 1978.

Darnell, J. E., et al. *Molecular Cell Biology*. New York, New York. Scientific American Books. pp. 581–583. 1986.

ORAL DOSAGE FORM OF BIOLOGICALLY ACTIVE PROTEINS

This is a continuation of U.S. application Ser. No. 07/994,076, filed Dec. 17, 1992, now abandoned, which is in turn is a continuation of U.S. application Ser. No. 07/709,622, filed Jun. 3, 1991, now abandoned.

BACKGROUND OF THE INVENTION

The present invention relates to oral dosage forms containing, as active ingredients, the biologically active proteins, granulocyte colony stimulating factor (G-CSF) and erythropoietin (EPO).

G-CSF is a hematopoietic factor which has been demonstrated to occur in the medium of cultures of human bladder carcinoma cell line 5637 (ATCC HT8-9) [Welte et al.: Proc. Natl. Acad. Sci. U.S.A., 82, 1526–1530 (1985)]. The DNA base sequence of the gene coding for this hematopoietic factor has been determined (Japanese Patent Application Laying-Out (KOHYO) No. 500636/88), thus making possible the production of G-CSF by the technique of genetic recombination.

G-CSF is effective in the treatment of common hematopoietic disorders, including hematopoietic disorders caused by chemotherapy or radiotherapy, and in bone marrow transplantation (Welte et al. supra).

Pharmaceutical preparations G-CSF with various stabilizers and additives for preventing its inactivation and adsorption to storage container walls have been the subject of numerous patent applications, e.g., Japanese Patent Application Laid-Open (KOKAI) No. 146826/88, for a preparation with an added surfactant; Japanese Patent Application Laid-Open (KOKAI) No. 146827/88 for a preparation with an added saccharide; Japanese Patent Application Laid-Open (KOKAI) No. 146828/88 for a preparation with an added high moleuclar weight compound; Japanese Patent Application Laid-Open (KOKAI) No. 146829/88 for a preparation with an added amino acid, sulfurated reducing agent, or antioxidant; and, Japanese Patent Application Laid-Open (KOKAI) No. 152326/88 for a preparation with an added protein. All these preparations, however, are in the form of injectable solutions.

A sustained-release preparation comprising G-CSF incorporated into a vehicle consisting of a biocompatible high polymer to prevent its inactivation and to extend the duration of its drug effects upon administration has been the subject of Japanese Patent Application Laid-Open (KOKAI) No. 91325/88. Furthermore, an enteric-coated preparation composed of G-CSF, a surfactant, a substance in a solid state at ordinary temperature and soluble in organic solvents, and an enteric material, designated for oral administration, has been reported [see, PCT Laid-Open Official Gazette (KOKAI-KOHO WO90/01329)].

Erythropoietin (EPO) is a hematopoietic glycoprotein hormone with an approximate molecular weight of 34,000 which is largely produced in and secreted by the kidneys and which functions to stimulate the differentiation of erythroblastic precursor cells into erythrocytes. EPO has been shown to be useful in erythropoietic therapy, represented by therapy for anemia, in man and other mammals.

Processes for obtaining EPO from natural sources, such as from urine of patients with aplastic anemia are known [Miyake et al., *J. Biol. Chem.*, 252(15): pp. 5558–5564 (1977)]. Such methods, however, provide only a limited supply because of low yields and are therefore not suitable for industrial, large-scale production. Processes for production of EPO in high yields utilizing recombinant DNA techniques have been described. See, Japanese Patent Publication (KOKOKU) No. 17156/90 and U.S. Pat. No. 4,703,008.

Pharmaceutical preparations containing EPO have been the subject of patent applications, e.g., Japanese Patent Application Laid Open (KOKAI) No. 91131/86 and (KOKAI) No. 97229/86 for preparations with serum albumin, dextran or polyethylene glycol added to EPO for its stabilization or prevention of its adsorption to storage container walls and KOKAI No. 89627/87 for an intranasal preparation consisting of EPO and an aqueous and/or non-aqueous medium containing a surfactant.

Biologically active proteins are generally liable to be degraded by gastric acid and by enzymes in the gastrointestinal lumen or wall, and it is extremely difficult to have them absorbed from the digestive tract because of their molecular sizes and complicated molecular structures. Their clinical application has therefore been limited to parenteral administration by intravenous, subcutaneous or intramuscular injection. Parenteral administration entails problems of inflicting pain on the patient, of causing damage to the tissue at the site of injection, and of not readily permitting self-medication. Various proposals have been made for alternative methods of administration, including for example, intranasal administration [*Pharm. Res.*, 21:105 (1989)], oral administration [*Res. Commun. Pathol. Pharmacol.*, 63:53 (1989)], tracheal administration [*Diabetes*, 20:552 (1971)], transdermal administration [*J. Pharm. Sci.*, 78:376 (1989)] and rectal administration [*J. Pharm. Pharmacol.*, 33:334 (1981)]. These alternative methods all entail additional problems and none has proven to be of significant practical use.

The above problems associated with administration of biologically active proteins apply to G-CSF and EPO as well. Oral administration of these proteins would be greatly preferred for purposes of simplicity, avoidance of pain to the patient and clear potential for self-medication. However, proposals for oral administration of these substances have been extremely rare compared to proposals for other methods of dosing. See, e.g., *Chem. Pharm. Bull*, 30:2245 (1982) describing preparations in which the active ingredient is enclosed in liposomes; Japanese Patent Application (KOKUGAN) No. 190833/88 wherein the active ingredient is entrapped in microcapsules; and, *Science*, 233:1081 (1986) describing an active ingredient coated with azoaromatic copolymer.

Thus, there continues to exist a significant need in the art for new preparations of G-CSF or EPO suitable for oral administration with consequent obviation of the problems associated with parenteral administration.

SUMMARY OF THE INVENTION

Provided by the present invention are novel pharmaceutical preparations that allow for efficient absorption of G-CSF or EPO from the gastrointestinal tract and novel methods for manufacturing such preparations. The oral preparations provided by the present invention are characterized by comprising G-CSF or EPO, surfactant(s), fatty acid(s) and enteric material(s). Various aspects and advantages of the present invention will be apparent upon consideration of the following detailed description of illustrative embodiments thereof, reference being made to FIGS. 1 through 4 which provide graphic illustrations of the results of time course studies of leukocyte and neutrophil formation upon administration of preparations of the invention as described in Experiments 1 through 4, respectively.

DETAILED DESCRIPTION OF THE INVENTION

Figure 1:
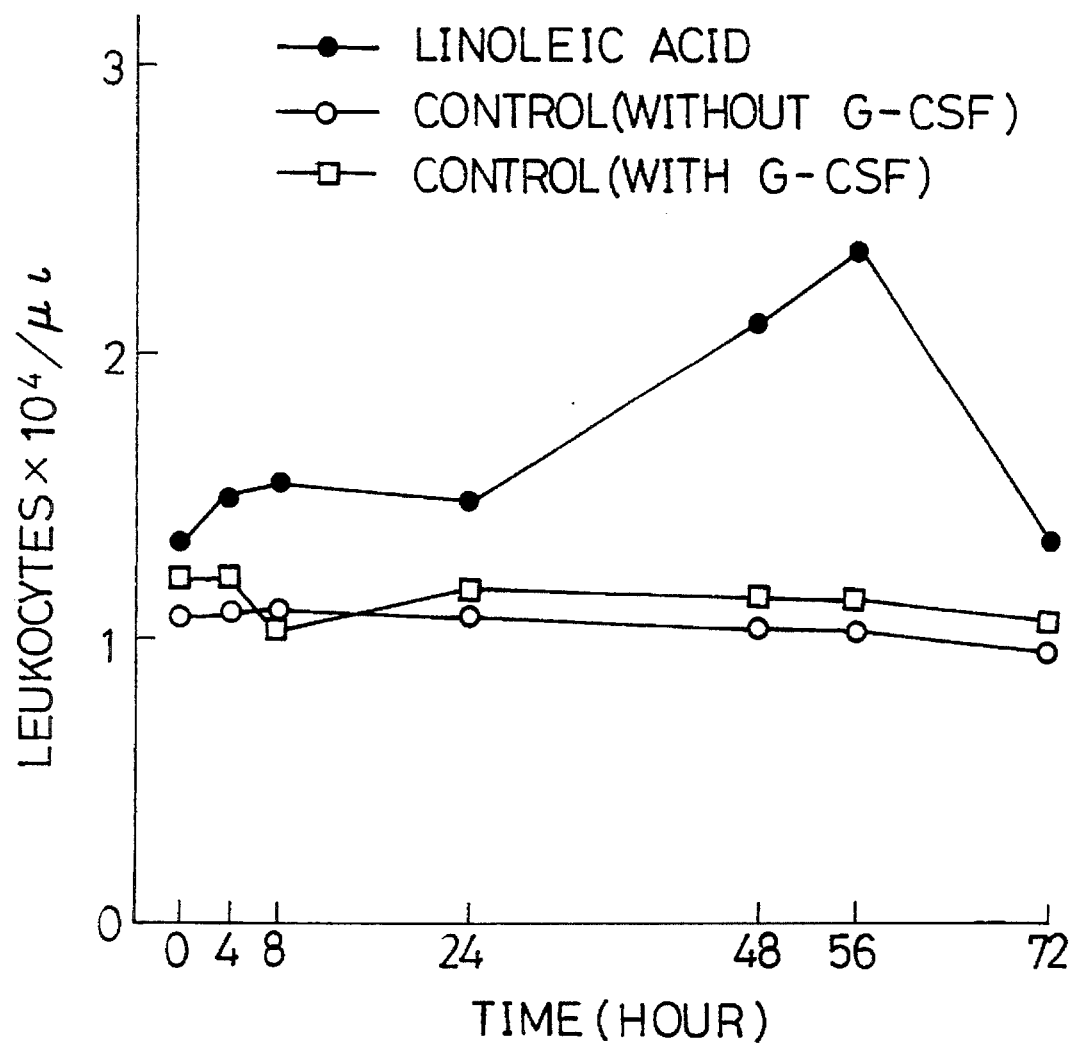
FIG. 1 depicts the total leukocyte counts in serial blood samples drawn at different time points from beagles after oral dosage in a form containing G-CSF and linoleic acid as prepared in Example 1.

G-CSF for use according to the present invention is preferably obtained as a product of the genetic transformation of a suitable host cell with a DNA sequence encoding G-CSF. More preferably, human G-CSF possessing substantially the amino acid sequence as set out in SEQ ID No: 1, with or without the initial methionyl residue, and produced by *Escherichia coli* via genetic recombination is used. The term "substantially" here denotes that the amino acid sequence either is identical with that of natural human G-CSF or contains one or more amino acid alterations (i.e., deletion, addition, insertion and displacement) which do not bring forth any detrimental functional dissimilarity to natural G-CSF. Illustratively, a recombinant human G-CSF with an amino acid sequence including a N-terminal methionine is most preferred for use in preparations of the invention and may be obtained in accordance with the disclosure of Japanese Patent Application Laying-Out (TOKUHYO) No. 500636/88.

The EPO for use in the present invention includes not only those materials naturally produced in humans and other mammals such as monkeys but also polypeptides which possess the biological activity of natural EPO and are obtained by recombinant DNA techniques as disclosed in TOKKO No. 17156/90 and analogues thereof possessing the biological activity of natural EPO. The EPO used in this invention is preferably a human species EPO.

Surfactants useful in practice of the present invention include anionic surfactants such as sodium lauryl sulfate, dioctyl sodium sulfosuccinate and dioctyl sodium sulfonate, cationic surfactants such as benzalkonium chloride and benzethonium chloride, and nonionic surfactants such as lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methylcellulose and carboxymethyl cellulose. One or a mixture of two or more of these surfactants may be used. Preferably, these surfactants are added in a ratio of between 0.1 and 1000 parts by weight to one part by weight of G-CSF and more preferably in a ratio between 0.1 and 500 parts by weight to one part by weight G-CSF. Surfactants are preferably added in a ratio of between 0.05 to 800 mg per 100,000 IU of IPO and more preferably in a ratio between 0.05 to 400 mg per 100,000 IU of EPO.

Fatty acids useful in practice of the present invention include those contained in edible plants such as oleic acid, linoleic acid and linolenic acid, of which one or a mixture of two or more is used. Preferably, these fatty acids are added in a ratio of between 0.1 and 1000 parts by weight to one part by weight of G-CSF and more preferably in a ratio of between 0.1 and 500 parts by weight to one part by weight G-CSF. Fatty acids are preferably added in a ratio between 0.05 and 800 mg per 100,000 IU of EPO and more preferably they are added in a ratio between 0.05 to 400 mg per 100,000 IU of EPO. Among these fatty acids, oleic acid and linoleic acid are especially preferable.

Enteric materials useful in practice of the invention include cellulose acetate phthalate, methyl acrylate-methacrylate copolymer, carboxymethylcellulose, hydroxypropyl methylcellulose phthalate and hydroxypropyl methylcellulose acetate succinate, of which one or a mixture of two or more is used. The enteric materials may take the form of enteric capsules, enteric coating and the like.

In the present invention, excipients are used when deemed necessary. The excipients used in this invention include starches, sugars, inorganic substances, organic acids, celluloses, synthetic and semisynthetic polymers, amino acids and the like. The starches include corn starch, wheat starch, potato starch and the like. The sugars include lactose, glucose, saccharose, fructose, D-sorbitol, D-mannitol, inositol, sucrose and the like. The inorganic substances include magnesium stearate, calcium phosphate, calcium hydrogen phosphate, precipitated calcium carbonate, sodium hydrogen carbonate, magnesium carbonate, sodium chloride, calcium sulfate and so forth. The organic acids include succinic acid, tartaric acid, citric acid, fumaric acid, maleic acid, malonic acid, glutaric acid, adipic acid, malic acid, gluconic acid, glucuronic acid and the like. The celluloses include microcrystalline cellulose, methylcellulose, ethylcellulose, hydroxyethyl cellulose, hydroxypropyl cellulose, carboxypropyl cellulose, carboxymethyl cellulose sodium and so forth. The synthetic and semisynthetic polymers include polyvinyl alcohol, carboxyvinyl polymer, polyethylene glycol, polyvinylpyrrolidone, sodium polyacrylate and the like. The amino acids include L-arginine, D,L-methionine, L-phenylalanine, L-glutamic acid and so forth.

In the oral preparations provided by the present invention, absorption of the principal ingredient, the biologically active protein, from the gastrointestinal tract is especially enhanced by adding one or more fatty acids to the drug composition. This is considered to be due to synergistic actions of fatty acid and surfactant on the gastrointestinal mucosa with a consequent increase in absorbability of the biologically active protein, or due to formation of a complex with increased absorbability through combined actions of fatty acid and surfactant upon the bioactive protein.

The following procedures are considered practicable as the method for manufacturing the oral drug preparations provided by this invention. For example, a surfactant and a fatty acid are dissolved in a buffer solution or distilled water and sonicated. To this solution, a solution of G-CSF or EPO is added and, when necessary, an excipient is also added; the resultant mixture is mixed by stirring at low temperature. The solution obtained is then lyophilized into a powder. An excipient is added to the powder if necessary, and, after mixing, the mixture is sieved to an even grain size and filled in enteric capsules. In another method, a surfactant and a fatty acid are dissolved in a buffer solution or distilled water. To the resulting solution, a bulk solution of the biologically active protein is added and, if necessary, an excipient is also added, followed by stirring at low temperature. The solution obtained is then lyophilized into powder. An excipient is added to the powder if necessary, and the resulting mixture is sieved to even grain sizes and formed into tablet. The granules are enteric-coated and filled in hard gelatin capsules. Alternatively, an excipient is added to the powder if necessary, and the resulting mixture is sieved into granules of even grain sizes.

Organic solvents may be used in manufacturing the oral dosage forms provided by the present invention. Preferably, however, a buffer solution or distilled water is used in order to avoid inactivation of the principal ingredient, G-CSF or EPO, as well as to eliminate the influence of residual solvents. Furthermore, it is preferable to avoid thermal treatment in manufacturing process as above-described, in order to minimize inactivation of G-CSF or EPO. Lyophilization is not an essential process in the manufacturing of the oral dosage form provided by the present invention but is effective to provide high contents of the principal ingredient in the pharmaceutical preparations.

The following methods are practicable for the manufacturing of the enteric capsules. For example, an enteric material is dissolved in an organic solvent or dispersed in distilled water, and (hard or soft) capsules are immersed in or sprayed with the resulting solution and then allowed to dry. In another method, an enteric material is dissolved in an organic solvent or dispersed in distilled water, and capsule body molds and cap molds are immersed in the resulting solution, followed by drying and removal of formed enteric material capsules from the molds. In another method, an enteric material is dissolved in an organic solvent or dispersed in distilled water, and outer parts of hard gelatin capsule bodies and caps are immersed in the resulting solution and then dried. The dried outer parts were placed in distilled water to eliminate inner gelatin, followed again by drying to obtain enteric capsules.

The following examples will serve as further embodiments to illustrate the present invention.

Example 1

0.20 g of polyoxyethylene hydrogenated castor oil 60 and 0.28 g of linoleic acid were dissolved in 100 ml of distilled water and sonicated. To this solution, 200 ml of a G-CSF solution (0.50 mg/ml) were added and the resultant mixture was stirred overnight in a cold room, followed by lyophilization to obtain a homogeneous freeze-dried preparation.

4.0 g of hydroxypropyl methylcellulose phthalate were dissolved in 10 ml of a methanol-methylene chloride mixture (3:10), and outer parts of hard gelatin capsule bodies and caps were then immersed in the resultant solution and, subsequently, thoroughly dried.

The dried outer parts were placed in distilled water to remove inner gelatin, and dried again to obtain enteric capsules. The above-described yophilized preparation was filled in these enteric capsules. Besides, an enteric capsule preparation of G-CSF was prepared in the same manner as above but without the addition of linoleic acid.

Example 2

0.40 g of polyoxyl 40 stearate and 0.2 g of oleic acid were dissolved in 100 ml of distilled water and sonicated. 200 ml of a G-CSF solution (0.50 mg/ml) and 1.0 g of lactose were added to this solution, and the resultant mixture was stirred overnight in a cold room, followed by lyophilization to obtain a homogeneous freeze-dried preparation. This preparation was made into granules with the addition of 0.10 g of hydroxypropyl cellulose, and filled in enteric capsules which had been prepared in the same manner as in Example 1.

Example 3

0.50 g of polyoxy 40 stearate and 0.20 g of linoleic acid were dissolved in 100 ml of citrate buffer solution and sonicated. To this solution, 100 ml of a G-CSF solution (2.0 mg/ml), 0.10 g of L-arginine and 1.0 g of saccharose were added, and the resulting mixture was stirred overnight in a cold room, followed by freezedrying to obtain a homogeneous lyophilized preparation. To this preparation 0.10 g of succinic acid, 0.10 g of microcrystalline cellulose, and 0.10 g of magnesium stearate were added, mixed, and formed into tablets. The tablets were enteric-coated by spraying with a hydroxypropyl methylcellulose acetate succinate suspension and subsequent drying.

Example 4

0.40 g of sucrose fatty acid ester and 0.10 g of linoleic acid were dissolved in 100 ml of citrate buffer solution and sonicated. To this solution, 200 ml of a GCSF solution (2.0 mg/ml) and 1.0 g of lactose were added and stirred overnight in a cold room, and the mixture was freeze-dried to obtain a homegeneous lyophilized preparation. This preparation was made into granules with the addition of 0.1 g of hydroxypropyl cellulose. The granules were enteric-coated by spraying with a hydroxypropyl methylcellulose acetate succinate suspension and subsequent drying, and filled in hard gelatin capsules.

Example 5

0.40 g of sucrose fatty acid ester and 0.30 g of linoleic acid were dissolved in 100 ml of distilled water and sonicated. To this solution, 200 ml of a solution of EPO ($25 \times 10^4$ IU/ml) were added, and the mixture was stirred overnight in a cold room and freeze-dried to obtain a homogeneous lyophilized preparation. To this preparation, 0.10 g of sodium phosphate was added, and the resulting mixture was filled in enteric capsules made of hydroxypropyl methylcellulose.

Example 6

A solution of 0.30 g of polyoxyl 40 stearate and 0.20 g of oleic acid in 100 ml of distilled water was prepared and subjected to ultrasonification. To this solution, 200 ml of a solution of EPO ($25 \times 10^4$ IU/ml) and 1.0 g of lactose were added, and the mixture was stirred overnight in a cold room and then freeze-dried to obtain a homogeneous lyophilized preparation. This preparation was sieved to an even grain size, mixed with 0.20 g of microcrystalline cellulose and 0.05 g of magnesium stearate, and formed into tablets. The tablets were enteric-coated by spraying with a carboxymethylcellulose suspension and subsequent drying.

Example 7

0.30 g of polyoxyl 40 stearate are 0.20 g of linoleic acid were dissolved, with stirring, in 100 ml of distilled water and sonicated. To this solution, 200 ml a solution of EPO ($25 \times 10^4$ IU/ml), 1.0 g of D-mannitol and 0.10 g of L-arginine were added, stirred overnight in a refrigerator and freeze-dried to obtain a homogeneous lyophilized preparation. This preparation was made into granules with the addition of 0.10 g of hydroxypropyl cellulose, and the granules were enteric-coated by spraying with a hydroxypropyl methylcellulose acetate succinate suspension and subsequent drying, and filled in hard gelatin capsules.

Example 8

0.80 g of polyoxyl 40 stearate and 0.80 g of linoleic acid were dissolved in 100 ml of citrate buffer solution and sonicated. To 8 ml of this solution, 2 ml of G-CSF solution (73 mg/ml) was added and the resultant mixture was stirred overnight in a cold room to be a test solution.

In addition, three other test solutions were prepared according to the same procedure with the addition of oleic acid, linoleinic acid instead of linoleic acid or without the addition of fatty acid (for control solution).

Example 9

Five solutions containing 1.6 g of polyoxyl 40 stearate and 0 g, 0.4 g, 1.6 g, 3.2 g or 6.4 g of linoleic acid respectively in 100 ml of citrate buffer solution were prepared and sonicated. To 9 ml of each solution, 1 ml of G-CSF solution (20 mg/ml) was added and stirred overnight in a cold room to be a test solution.

Experiment 1

Male beagle dogs (13- to 15-months old) having been fasted for 20 hours (but allowed free access to water) were dosed orally with a drug dosage form of this invention containing linoleic acid prepared in Example 1 or with the same dosage form but not containing linoleic acid, at a dose of 2.2 mg/kg of G-CSF. Serial 0.5 ml blood samples were taken serially following the administration from the antebrachial vein of each dog. Each blood sample was collected in an EDTA-treated polystyrene tube and subjected to determination of blood total leukocyte count on an automated blood cell counter (Microcell Counter Sysmex CC-180A). Serial total leukocyte counts are shown in FIG. 1.

The total leukocyte count increased from 24 to 48 hours after oral administration of the drug dosage form containing linoleic acid provided by this invention, reached a peak at 56 hours post-dosing and returned to the initial level by 72 hours post-dosing. In contrast, no such pharmacological effect was observed in dogs receiving the drug preparation not containing linoleic acid or in those receiving a preparation not containing G-CSF (controls).

Experiment 2

Figure 2:
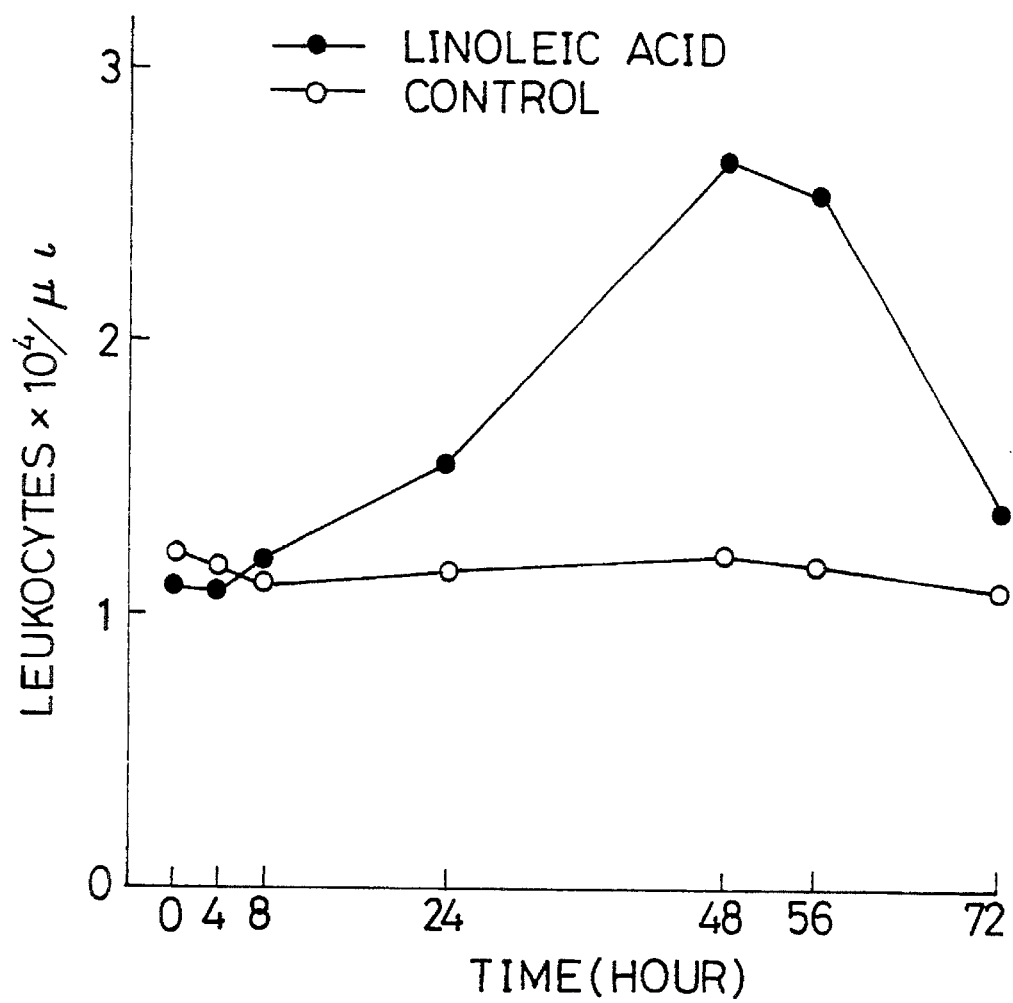
FIG. 2 depicts the total leukocyte counts in serial blood samples drawn at different time points from beagles after oral dosage in a form containing G-CSF and linoleic acid as prepared in Example 3.

Male beagle dogs (13- to 15-months old) having been fasted for 20 hours (but allowed free access to water) were dosed orally with a drug dosage form prepared in Example 3 at a dose of 2.0 mg/kg of G-CSF. 0.5 ml blood samples were taken serially following the administration from the antebrachial vein of each dog. Each blood sample was collected in an EDTA-treated polystyrene tube and subjected to determination of blood total leukocyte count on an automated blood cell counter (Microcell Counter Sysmex CC-180A). Serial total leukocyte counts are shown in FIG. 2.

The total leukocyte count increased from 8 to 24 hours after oral administration of the drug dosage form of this invention, reached a peak at 48 hours postdosing and returned to the initial level by 72 hours post-dosing. In dogs given a preparation not containing G-CSF (controls), on the other hand, no such pharmacologic effect was observed.

Experiment 3

Male rats (SD strain, 400–500 g body weight) were surgically inserted with a cannula from the stomach into the duodenum and were placed in separate cages for several days. After the effects of the operation were diminished test solutions prepared in Example 8 were administered into duodenum of rats through the cannula in a dose of 15 mg/kg of G-CSF. 0.3 ml blood samples were taken serially following the administration from the jugular vein of each rat.

Figure 3:
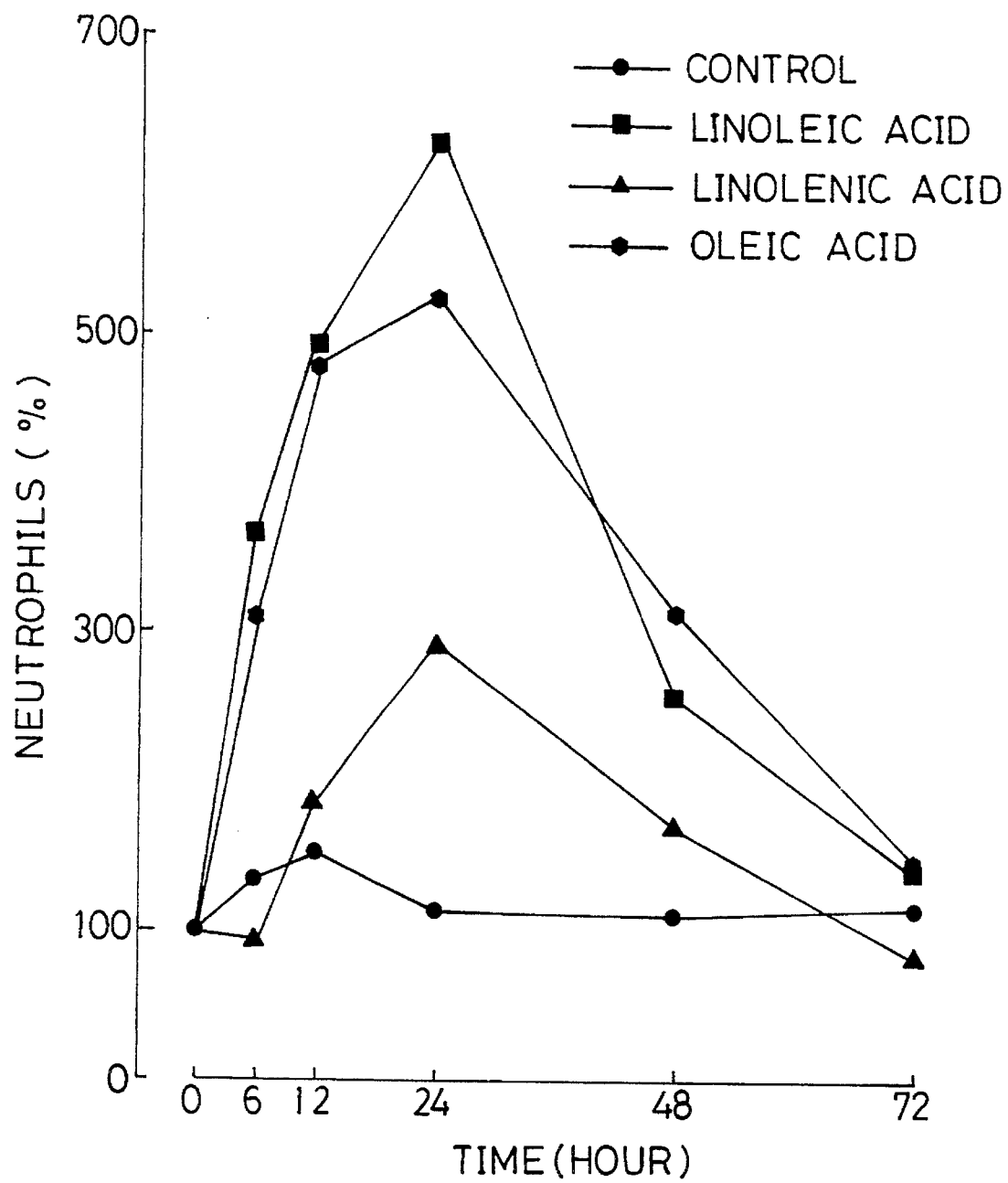
FIG. 3 depicts a comparison of the neutrophil percentages of total leukocyte counts in serial blood samples drawn from rats after surgical duodenal dosage with G-CSF in solutions prepared with different fatty acids according to Example 8.

Each blood sample was collected in a polystyrene tube treated with EDTA and one part of each sample was subjected to determination of blood total leukocyte count on an automated blood cell counter (Microcell Counter Sysmex CC-180A) and another part was used for determination of a ratio of neutrophils against total leukocyte from observing smears under microscope. Smears were prepared with spreading blood samples on slide glasses and subsequent staining. The neutrophil count in blood was then calculated from total leukocyte count and neutrophil ratio. Increasing ratios of the neutrophil count at each sampling point against the initial value are shown in the FIG. 3. A remarkable increase in the neutrophil count was observed from 6 to 48 hours after administration of a solution containing a fatty acid prepared according to this invention. In contrast, only a slight increase was seen at 6 hr and 12 hr after dosing of preparation without 10 fatty acid (control). Among fatty acids, preparations containing oleic acid or linoleic acid showed large pharmacological effects.

Experiment 4

Male rats (SD strain, 400–500 g body weight) were surgically inserted with a cannula from the stomach into the duodenum and were placed in separate cages for several days. After the effects of the operation were diminished, test solutions prepared in Example 9 were administered into duodenum of rats through the cannula in a dose of 2.4 mg/kg of G-CSF.

Figure 4:
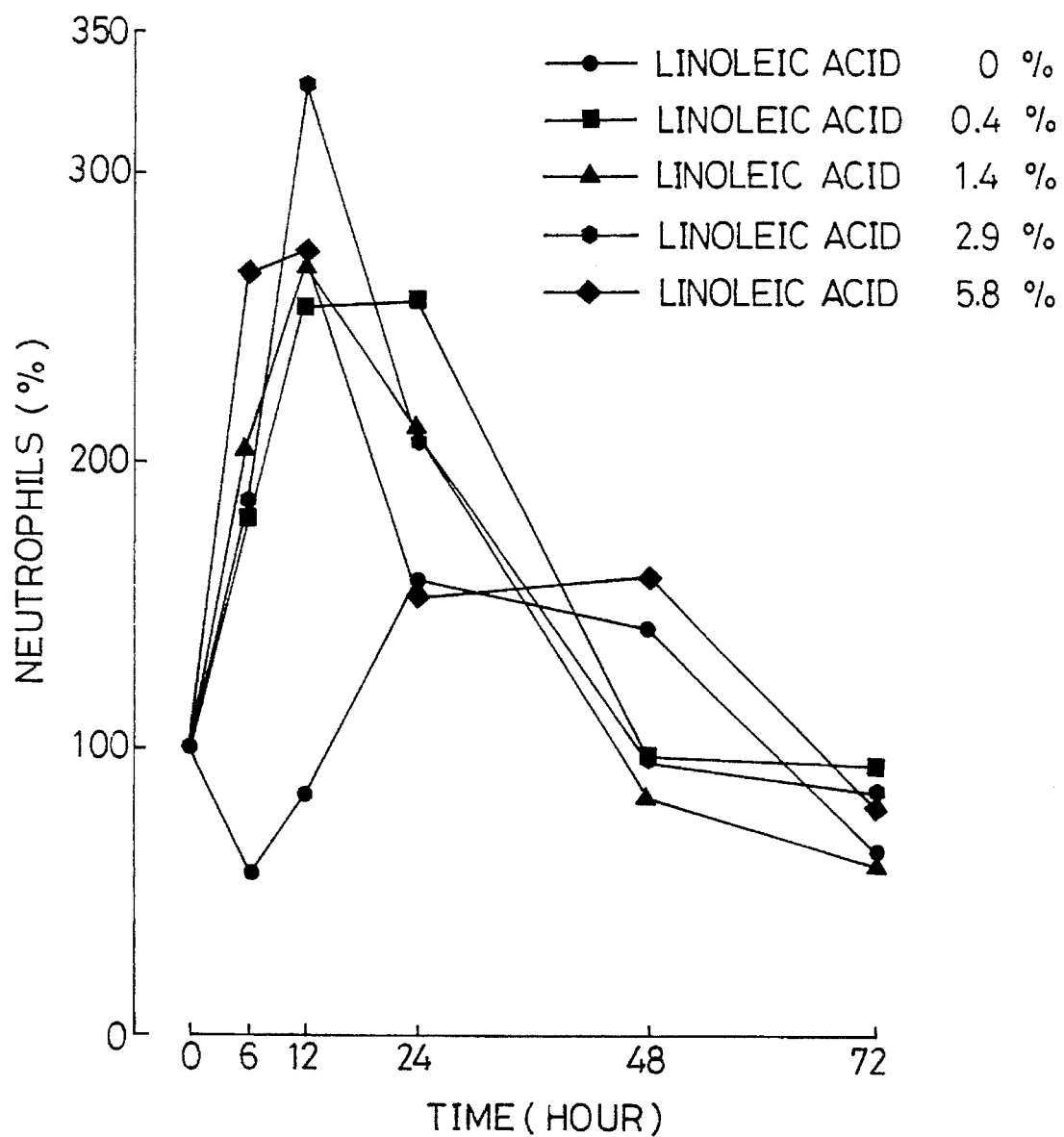
FIG. 4 depicts a comparison of the neutrophil percentages of total leukocyte counts in serial blood samples drawn from rats after surgical duodenal dosage with G-CSF in solutions prepared with different percentages of linoleic acid according to Example 9.

0.3 ml blood samples were taken serially following the administration from the jugular vein of each rat. Each blood sample was collected in a polystyrene tube treated with EDTA and one part of each sample was subjected to determination of blood total leukocyte count on an automated blood cell counter (Microcell Counter Sysmex CC-180A) and another part was used for determination of a ratio of neutrophils against total leukocyte from observing smears under microscope. Smears were prepared with spreading blood samples on slide glasses and subsequent staining. The neutrophil count in blood was then calculated from total leukocyte count and neutrophil ratio. Increasing ratios of the neutrophil count at each sampling point against the initial value are shown in the FIG. 4.

Remarkable increases in the neutrophil count were seen at 6 and 12 hours after administration of each preparation containing 0.4%, 1.4%, 2.9% or 5.8% of linoleic acid respectively produced by this invention. On the other hand, such pharmacological effect was almost never observed after administration of the preparation without linoleic acid. In this experiment, no significant difference was found with the addition of 0.4 to 5.8% of linolic acid (in a ratio between 1.9 and 45 parts by weight to one part by weight of G-CSF).

With the oral drug preparations provided by the present invention, therefore, inactivation of the principal ingredient during the process of pharmaceutical manufacturing has been shown to be avoided along with proven effects such as enhanced absorption of the principal ingredient from the intestinal tract particularly as a result of the addition of fatty acid to the drug composition. These factors not only lead to a potential for dosage reduction but also facilitate accurate dose control and increase the practical usefulness of the bioactive proteins in the form of oral preparations.

What is claimed is:

1. An oral dosage form comprising the components:
   (a) granulocyte colony stimulating factor or erythropoietin;
   (b) surfactant(s);
   (c) fatty acid(s); and
   (d) enteric material,
   wherein said components (a), (b) and (c) are mixed in liquid phase and lyophilized prior to combination with component (d).

2. The oral dosage form of claim 1 wherein said surfactant(s) comprise one or more anionic surfactants selected from the group consisting of sodium lauryl sulfate, dioctyl sodium sulfosuccinate and dioctyl sodium sulfonate.

3. The oral dosage form of claim 1 wherein said surfactant(s) comprise one or more cationic surfactants selected from the group consisting of benzalkonium chloride and benzethonium chloride.

4. The oral dosage form of claim 1 wherein said surfactant(s) comprise one or more nonionic surfactants elected from the group consisting of lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methylcellulose and carboxymethyl cellulose.

5. The oral dosage form of claim 1 comprising granulocyte colony stimulating factor and wherein said surfactant(s) are present in a ratio of between 0.1 to 1000 parts by weight surfactant per part by weight granulocyte colony stimulating factor.

6. The oral dosage form of claim 5 wherein said surfactant(s) are present in a ratio of between 0.1 to 500 parts by weight per part by weight granulocyte colony stimulating factor.

7. The oral dosage form of claim 1 comprising erythropoietin and wherein said surfactant(s) are present in a ratio of between 0.05 to 800 mg surfactant per 100,000 IU erythropoietin.

8. The oral dosage form of claim 7 wherein said surfactant(s) are present in a ratio of between 0.05 to 400 mg surfactant per 100,000 IU erythropoietin.

9. The oral dosage form of claim 1 wherein said fatty acid(s) comprise one or more fatty acids selected from the group consisting of oleic acid, linoleic acid and linolinic acid.

10. The oral dosage form of claim 1 comprising granulocyte colony stimulating factor and wherein said fatty acid(s) are present in a ratio of between 0.1 to 1000 parts by weight fatty acid per part by weight granulocyte colony stimulating factor.

11. The oral dosage form of claim 10 wherein said fatty acid(s) are present in a ratio of between 0.1 and 500 parts by weight fatty acid per part by weight granulocyte colony stimulating factor.

12. The dosage form of claim 1 comprising erythropoietin and wherein said fatty acid(s) are present in a ratio of between 0.05 to 800 mg fatty acid per 100,000 IU erythropoietin.

13. The dosage form of claim 12 wherein said fatty acid(s) are present in a ratio of between 0.05 and 400 mg fatty acid per 100,000 IU erythropoietin.

* * * * *

UNITED STATES PATENT AND TRADEMARK OFFICE
CERTIFICATE OF CORRECTION

PATENT NO.   :   5,597,562

DATED        :   January 28, 1997

INVENTORS    :   Nomura *et al.*

It is certified that error appears in the above-identified patent and that said Letters Patent is hereby corrected as shown below:

Column 1, line 27 replace "Supra" with "<u>Supra</u>"

Column 1, line 65 replace "*J. Biol. Chem. 252(15)*" with

Column 2, line 27 replace "*Pharm. Res.*, 21" with "<u>Pharm. Res., 21</u>"

Column 2, line 28 replace "*Res. Commun. Pathol. Pharmacol.*, 63" with "<u>Res. Commun. Pathol. Pharmacol., 63</u>"

Column 2, line 29 replace "*Diabetes*, 20" with "<u>Diabetes, 20</u>"

Column 2, line 30 replace "*J. Pharm. Sci.*, 78" with "<u>J. Pharm. Sci., 78</u>"

Column 2, line 31 replace "*J. Pharm. Pharmacol.*, 33" with "<u>J. Pharm. Pharmacol., 33</u>"

Column 2, line 43 replace "*Chem. Pharm. Bull*, 30" with "<u>Chem. Pharm. Bull, 30</u>"

Column 2, line 46 replace "*Science*, 233" with "<u>Science, 233</u>"

UNITED STATES PATENT AND TRADEMARK OFFICE
CERTIFICATE OF CORRECTION

PATENT NO. : 5,597,562

DATED : January 28, 1997

INVENTORS : Nomura et al.

It is certified that error appears in the above-identified patent and that said Letters Patent is hereby corrected as shown below:

Column 3, line 34 repalce "Escherichia coli" with "Escherichia coli"

Column 5, line 56 replace "yophilized" with "lyophilized"

Column 9, line 65 replace "elected" with "selected"

Signed and Sealed this

Fifth Day of August, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 175 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Met Thr Pro Leu Gly Pro Ala Ser Ser Leu Pro Gln Ser Phe Leu Leu
 1               5                  10                  15

Lys Cys Leu Glu Gln Val Arg Lys Ile Gln Gly Asp Gly Ala Ala Leu
             20                  25                  30

Gln Glu Lys Leu Cys Ala Thr Tyr Lys Leu Cys His Pro Glu Glu Leu
         35                  40                  45

Val Leu Leu Gly His Ser Leu Gly Ile Pro Trp Ala Pro Leu Ser Ser
     50                  55                      60

Cys Pro Ser Gln Ala Leu Gln Leu Ala Gly Cys Leu Ser Gln Leu His
 65                  70                      75                  80

Ser Gly Leu Phe Leu Tyr Gln Gly Leu Leu Gln Ala Leu Glu Gly Ile
                 85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```